United States Patent [19]

Yokoi et al.

[11] Patent Number: 4,584,377

[45] Date of Patent: Apr. 22, 1986

[54] NOVEL FREDERICAMYCIN A DERIVATIVES

[75] Inventors: Koichi Yokoi, Kashiwa; Hiroshi Hasegawa, Yachiyo; Tadashi Narita, Chiba; Takemitsu Asaoka, Narita; Kenichi Kukita, Kashiwa; Seiji Ishizeki, Yachiyo; Toshiaki Nakashima, Shisuimachi, all of Japan

[73] Assignee: SS Pharmaceutical Co., Ltd., Tokyo, Japan

[21] Appl. No.: 639,113

[22] Filed: Aug. 9, 1984

[30] Foreign Application Priority Data

Aug. 18, 1983 [JP] Japan ............................. 58-150522
Sep. 8, 1983 [JP] Japan ............................. 58-165489
Sep. 9, 1983 [JP] Japan ............................. 58-166082

[51] Int. Cl.$^4$ ........................................... C07D 221/18
[52] U.S. Cl. ........................................................ 546/15
[58] Field of Search ........................................... 546/15

[56] References Cited

PUBLICATIONS

Misra et al., "J. Am. Chem. Soc." (1982), vol. 104, pp. 4478–4479.
Pandey et al., J. Antibiotics vol. 34, pp. 1389–1401, (1981).
Warnick-Pickle et al., J. Antibiotics vol. 34, pp. 1402–1407, (1981).

Primary Examiner—Robert T. Bond
Attorney, Agent, or Firm—Oblon, Fisher, Spivak, McClelland & Maier

[57] ABSTRACT

Disclosed herein are Fredericamycin A derivatives, each, represented by the following general formula (I):

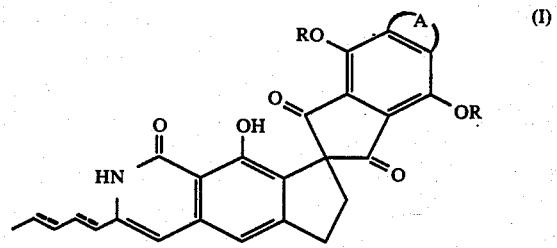

wherein R means a hydrogen atom or acyl group, A denotes

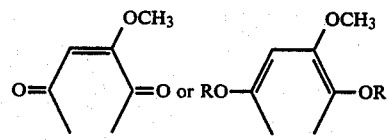

and dotted bonds are optional, with a proviso that when A is

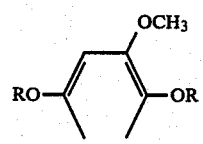

or the dotted bonds are contained, R is other than hydrogen atom. They have excellent antibacterial and antitumor activities and at the same time, are extremely stable compared with Fredericamycin A.

12 Claims, 8 Drawing Figures

NOVEL FREDERICAMYCIN A DERIVATIVES

BACKGROUND OF THE INVENTION

1. Field of the Invention

This invention relates to novel Fredericamycin A derivatives.

2. Description of the Prior Art

It has hitherto been known that an antitumor antibiotic represented by the following formula (II):

(II)

Fredericamycin A (NSC-305263) can be isolated from a culture of *Streptomyces griseus* FCRC-48 ["J. Antibiotics", 34, 1389–1401(1981); ibid, 34, 1402–1407(1981)].

Fredericamycin A is however accompanied by such problems that its antibacterial activities are weak and its stability is low.

SUMMARY OF THE INVENTION

The present inventors have accordingly synthesized various derivatives of Fredericamycin A and studied their pharmacological effects and stability with a view toward overcoming the above-mentioned drawbacks of Fredericamycin A. As a result, it has been found that Fredericamycin A derivatives, which are each represented by the following formula (I):

(I)

wherein R means a hydrogen atom or acyl group, A denotes and dotted bonds are optional, with a proviso that when A is or the dotted bonds are contained, R is other than hydrogen atom, has excellent antibacterial and antitumor activities and at the same time, are extremely stable compared with Fredericamycin A, leading to completion of this invention.

Therefore, an object of this invention is to provide Fredericamycin A derivatives (I) which are useful as antibacterial agents and antitumor drugs.

In one aspect of this invention, there is thus provided a Fredericamycin A derivative represented by the following general formula (I):

(I)

wherein R means a hydrogen atom or acyl group, A denotes and dotted bonds are optional, with a proviso that when A is or the dotted bonds are contained, R is other than hydrogen atom.

The above and other objects, features and advantages of the present invention will become apparent from the following description and the appended claims, taken in conjunction with the accompanying drawings.

DETAILED DESCRIPTION OF THE INVENTION

Figure 1:
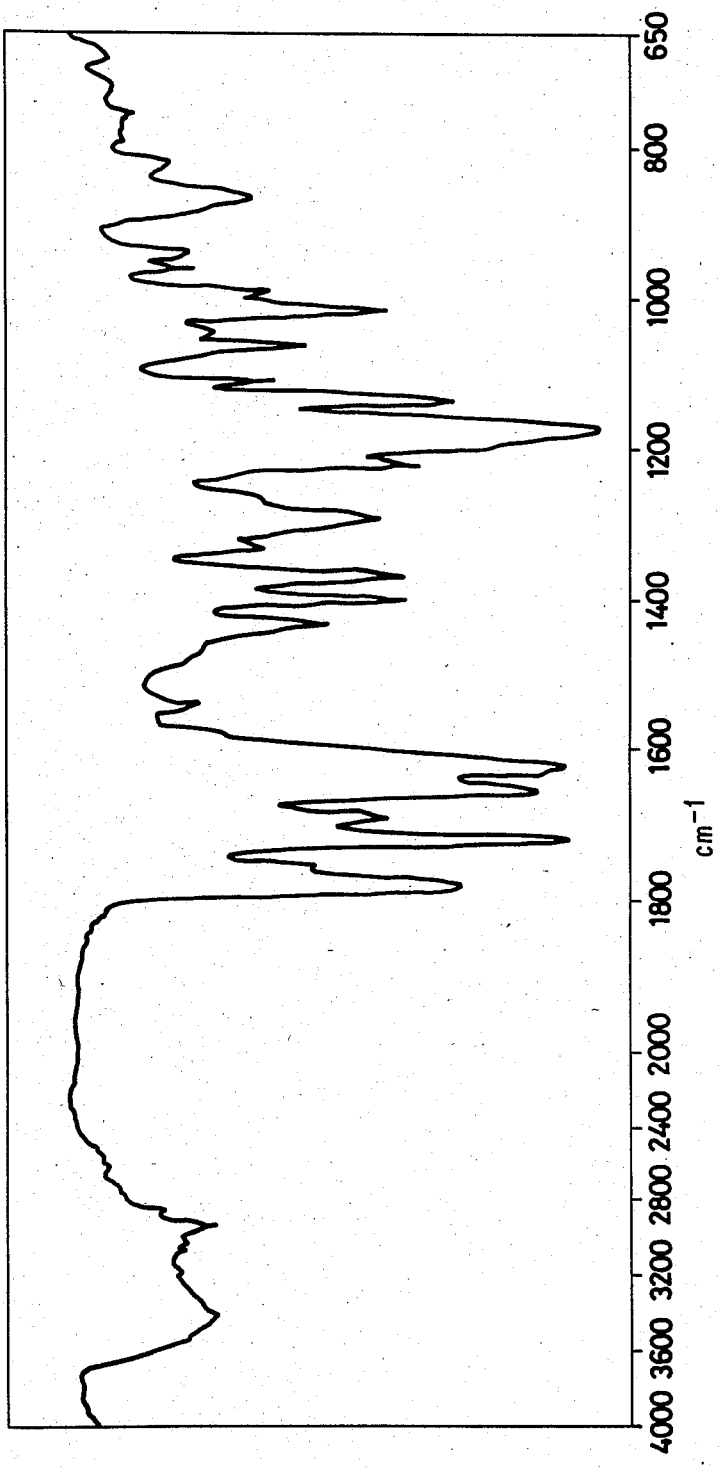
FIG. 1 and FIG. 2 shows an IR and $^1$H-NMR spectra of Compound 1, respectively.

The Fredericamycin A derivatives (I) according to this invention may further be classified roughly into the following three groups of compounds:

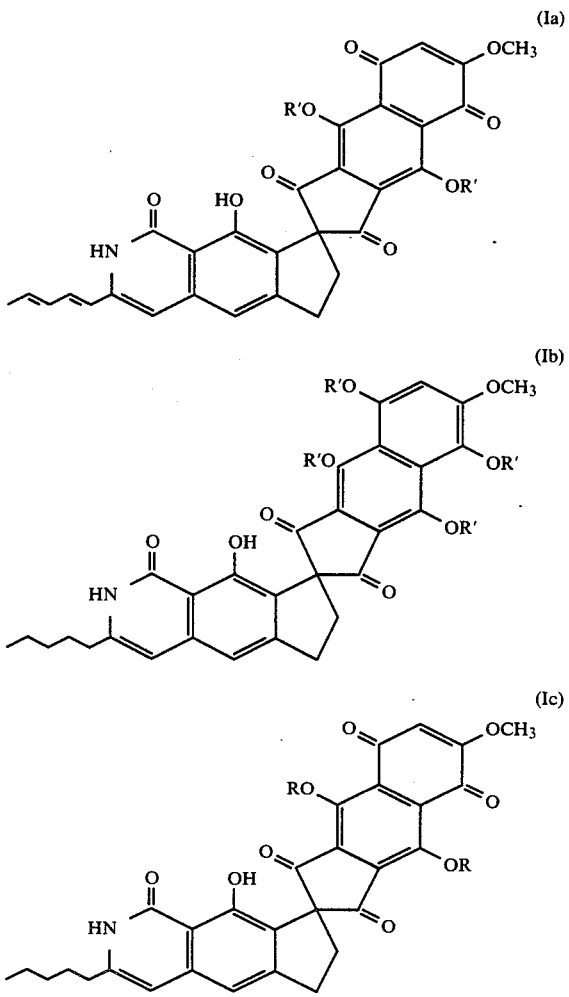

wherein R has the same meaning as defined above, and R' denotes an acyl group.

The Fredericamycin A derivatives (I) of this invention may be prepared by either one of the following processes:

PROCESS 1

The Fredericamycin A diacyl derivatives (Ia) may individually be prepared by reacting, in accordance with the usual acylation method, Fredericamycin A (II) with a carboxylic acid represented for example by $R_1$—COOH wherein $R_1$ means an alkyl group or a substituted or unsubstituted phenyl group, an alkyl group containing 1-18 carbon atoms is preferred as the alkyl group, and a straight-chain or branched, lower alkyl group containing 1-6 carbon atoms, a lower alkoxy group containing 1-6 carbon atoms or a halogen atom such as chlorine, bromine, fluorine or iodine may be mentioned as each substituent group of the phenyl group, or a reactive derivative thereof. An acid halide, acid anhydride, mixed acid anhydride, activated ester or the like may be used as the reactive derivative. In the above process, it is preferred to conduct the reaction in a solvent such as pyridine for example, at a temperature of 0°-4° C. and for 2-48 hours, using an acylating agent in a mole equivalent 3-10 times the Fredericamycin A. It is also possible to react Fredericamycin A directly with the carboxylic acid by using a condensing agent such as dicyclohexylcarbodiimide (DCC) or the like.

PROCESS 2

The leucotetraacyltetrahydrofredericamycin A represented by the formula (Ib) out of the compounds of this invention may each be prepared by reducing Fredericamycin A (II) with a suitable reducing agent and then acylating the thus-reduced Fredericamycin A. The reduction is carried out using a usual reducing agent. It is preferred for example to subject Fredericamycin A (II) to catalytic reduction in the presence of a catalyst such as palladium-bearing activated carbon or platinum oxide while blowing hydrogen gas thereinto. The acylation is conducted by reacting the thus-obtained reduced intermediate with a carboxylic acid represented for example by $R_1COOH$ wherein $R_1$ has the same meaning as defined above or its reactive derivative in accordance with the usual acylation method. As the reactive derivative of the carboxylic acid, an acid halide, acid anhydride, mixed acid anhydride, activated ester or the like may be employed. Here, it is preferred to conduct the reaction in a solvent such as pyridine for example, at room temperature and for 1-48 hours, using the carboxylic acid derivative in a mole equivalent 5-20 times based on the above-mentioned reduced intermediate. It is also feasible to react the reduced intermediate directly with the carboxylic acid by using a condensing agent such as DCC.

PROCESS 3

The tetrahydrofredericamycin A derivatives represented by the formula (Ic) out of the compounds of this invention may be prepared by reducing Fredericamycin A (II) with a suitable reducing agent and then either partially oxidizing or acylating the thus-reduced intermediate. The reduction is carried out using a usual reducing agent. It is preferred to subject Fredericamycin A (II) to catalytic reduction in the presence of a catalyst such as palladium-bearing activated carbon or platinum oxide while blowing hydrogen gas therein. The partial oxidation can be carried out by subjecting, after the reduction, the reduced intermediate for example to air oxidation or the like in a suitable solvent. On the other hand, the acylation may be effected by reacting the thus-obtained compound with a carboxylic acid represented for example by $R_1COOH$, wherein $R_1$ has the same meaning as defined above or its reactive derivative in accordance with the usual acylation method. As the reactive derivative of the carboxylic acid, there may be used an acid halide, acid anhydride, mixed acid anhydride, activated ester or the like. Here, it is preferred to conduct the reaction in a solvent such as pyridine for example, at a temperature of 0°-4° C. and for 2-48 hours, using the carboxylic acid derivative in a mole equivalent 3-10 times the tetrahydrofredericamycin A [R=H in the formula (Ic)]. It is also possible to react tetrahydrofredericamycin A directly with the above-described carboxylic acid by using a condensing agent such as DCC.

With respect to certain representative compounds of this invention which had been obtained in the above-described manner, their antibacterial activities and antitumor activities were tested. The test gave the following results.

(1) ANTIBACTERIAL ACTIVITIES (1) Table 1 shows the minimum inhibitory concentration (MIC) of the representative compounds of this invention against various microorganisms. It should be noted that the MIC of Fredericamycin A was 100 μg/ml or more for each of the tested microorganism.

Culture conditions for the test microorganisms:

Inoculum size: $1 \times 10^6$ cells/ml. In the case of bacteria, each bacterium was cultured at 37° C. for 18–20 hours on a Mueller-Hinton agar (product of Difco Corp.). In the case of yeasts and molds, each microorganism was cultured at 28° C. for 120 hours on a glucose-peptone agar.

TABLE 1

| Test microorganism | Minimum inhibitory concentration MIC(μg/ml) | |
|---|---|---|
| | Compound 1 | Compound 18 |
| Bacillus subtilis ATCC 6633 | 0.39 | 50 |
| Staphylococcus aureus FDA 209P | 50 | |
| Staphylococcus aureus TERAGIMA | 12.5 | |
| Staphylococcus aureus Smith | 6.25 | 25 |
| Staphylococcus epidermidis ATCC 12228 | 0.10 | 0.78 |
| Sarcina lutea ATCC 9341 | 0.39 | 25 |
| Streptococcus faecalis IFO 12964 | 1.56 | 25 |
| Micrococcus lysodeikticus IFO 3333 | 0.78 | 25 |
| Escherichia coli 0-1 | >100 | >100 |
| Salmonella typhi TD | >100 | |
| Shigella flexneri 2b | >100 | |
| Pseudomonas aeruginosa IFO 13736 | >100 | >100 |
| Klebsiella pneumoniae ATCC 10031 | >100 | |
| Proteus vulgaris OXK | >100 | |
| Seratia marcescens NHL | >100 | |
| Candida albicans NHL 4019 | >100 | >100 |
| Saccharomyces ruxii 6507 | 0.39 | >100 |
| Aspergillus niger ATCC 9642 | 3.12 | >100 |
| Aspergillus oryzae IFM 4014 | 1.56 | |
| Penicillium chrysogenum ATCC 6010 | 0.78 | >100 |
| Trichophyton mentagrophytes QM 248 | 0.39 | >100 |
| Microsporum gypseum IFO 8231 | 0.39 | |
| Gibberella fujikuroi IAM 8046 | >100 | |
| Cladosporium fulvum IAM 5006 | 1.56 | |
| Fusarium moniliforme IAM 5062 | 50 | |
| Helmintsporium sesamum IAM 5012 | 0.78 | |
| Piricularia oryzae IAM 5016 | 0.05 | 0.78 |
| Debaryomyces Kloecheri IFO 0015 | 100 | >100 |

(2) The MIC of various Fredericamycin A derivatives are shown in Table 2. The culture conditions of the test microorganisms were the same as those employed above for the determination of antibacterial activities (1).

TABLE 2

| Fredericamycin A derivative | Test microorganism (MIC: μg/ml) | |
|---|---|---|
| | Staphylococcus epidermidis ATCC 12228 | Piricularia oryzae IAM 5016 |
| Compound 5 | 25 | 0.39 |
| Compound 7 | 25 | 1.56 |
| Compound 3 | 25 | 6.25 |
| Compound 10 | 12.5 | 1.56 |

(2) ANTITUMOR ACTIVITIES

Antitumor effects of some Fredericamycin A derivatives against Ehrlich carcinoma, Meth-A fibrosarcoma and mouse leukemia P-388 were tested in accordance with the following procedures. Antitumor effects against Ehrlich carcinoma and Meth-A fibrosarcoma are expressed by percentage of mean survival time of test and control animals. Antitumor effects against P-388 are expressed by percentage of median survival time of test and control animals.

Those results are shown in Table 3.

EXPERIMENT PROCEDURES (i) Ehrlich carcinoma:

$5 \times 10^6$ tumor cells were inoculated to ICR mice (♀, Clea Japan Inc.) intraperitoneally. Each tested compound was given intraperitoneally once a day for 10 days from 1 day after tumor inoculation.

(ii) Meth-A fibrosarcoma and mouse leukemia P-388:

$1 \times 10^6$ tumor cells were inoculated to CDF$_1$ mice (♂, Charles River Japan Inc.) intraperitoneally. Each tested compound was given intraperitoneally once a day for 10 days from 1 day after tumor inoculation.

TABLE 3

| Test compound | Dosage (mg/kg/day) | Ehrlich carcinoma | Meth-A fibrosarcoma | P-388 |
|---|---|---|---|---|
| Compound 1 | 0.125 | 147 | — | — |
| | 0.25 | 267 | 127 | — |
| | 0.5 | 295 | 191 | — |
| | 1.0 | — | 242 | — |
| Compound 2 | 0.5 | 120 | — | — |
| | 1.0 | over 168 | — | — |
| | 2.0 | over 229 | — | — |
| Compound 4 | 0.5 | over 282 | — | — |
| | 1.0 | over 288 | — | — |
| | 2.0 | 50 | — | — |
| Compound 5 | 0.5 | over 247 | — | — |
| | 1.0 | over 229 | — | — |
| | 2.0 | over 256 | — | — |
| Compound 7 | 0.5 | 104 | — | — |
| | 1.0 | 96 | — | — |
| | 2.0 | 194 | — | — |
| Compound 8 | 0.5 | 166 | — | — |
| | 1.0 | over 199 | — | — |
| | 2.0 | 97 | — | — |
| Compound 10 | 0.5 | 105 | — | — |
| | 1.0 | 171 | — | — |
| | 2.0 | over 202 | — | — |
| Compound 11 | 0.5 | over 139 | — | — |

TABLE 3-continued

| Test compound | Dosage (mg/kg/day) | Ehrlich carcinoma | Meth-A fibrosarcoma | P-388 |
| --- | --- | --- | --- | --- |
| | 1.0 | over 198 | — | — |
| | 2.0 | over 260 | — | — |
| Compound 12 | 2.0 | 116 | — | 142 |
| | 4.0 | 136 | — | 146 |
| | 8.0 | over 203 | — | 152 |
| Compound 17 | 0.125 | 187 | — | — |
| | 0.25 | 248 | 102 | — |
| | 0.5 | 250 | 129 | — |
| | 1.0 | — | 164 | — |
| | 2.0 | — | 232 | 130 |
| | 4.0 | — | — | 143 |
| | 8.0 | — | — | 152 |
| Compound 18 | 2.0 | 125 | — | 138 |
| | 4.0 | over 188 | — | 142 |
| | 8.0 | over 212 | — | 147 |

(3) STABILITY

The stability of some Fredericamycin A derivatives and Fredericamycin A in their aqueous solutions were tested in accordance with the following procedures. Results are shown in Table 4.

Experiment procedures:

The test compounds were individually dissolved in dimethylsulfoxide, followed by dilution of the resulting solutions with physiological saline to adjust the final concentrations of the test compounds and Fredericamycin to 10 μg/ml respectively. The thus-prepared test solutions were then subjected to high performance liquid chromatography after predetermined time intervals to measure the percentage remainders of the test compounds.

TABLE 4

| Test compound | Percentage remainder (%) | | | | | |
| --- | --- | --- | --- | --- | --- | --- |
| | 0 hr. | 3 hrs. | 6 hrs. | 24 hrs. | 48 hrs. | 72 hrs. |
| Compound 5 | 100 | 93.2 | 88.0 | 67.6 | 57.3 | 47.9 |
| Compound 12 | 100 | 99.0 | 98.3 | 97.1 | 95.7 | 94.4 |
| Compound 21 | 100 | 95.3 | 92.2 | 87.3 | 80.5 | 74.8 |
| Fredericamycin A | 100 | 78.9 | 64.0 | 38.1 | 27.3 | 18.4 |

The invention will hereinafter be described in the following Examples.

EXAMPLE 1

Dissolved in 20 ml of pyridine was 0.54 g (1.0 mmol) of Fredericamycin A, to which 1.02 g (10 mmol) of acetic anhydride dissolved in 5 ml of pyridine was added dropwise over about 30 minutes. The resulting mixture was stirred at 0° C. for 3 hours. The resultant liquid reaction mixture was poured into 200 ml of ice-cooled 2N hydrochloric acid, followed by an extraction with ethyl acetate. The ethyl acetate layer was washed successively with dilute hydrochloric acid and then with water, and was thereafter dried with anhydrous sodium sulfate. After filtration, the ethyl acetate was distilled off, and the residue was recrystallized from a mixed solvent of ethyl acetate and acetic acid to obtain 0.52 g of Fredericamycin A diacetate [R′=—COCH$_3$ in the formula (Ia); Compound 1] as yellowish brown crystals (yield: 83.5%).

Melting point: over 300°.

Mass M+ m/z: 623.

UV $\lambda_{max}^{EtOH}$nm(ε): 393(21,200), 374(32,100), 359(27,200), 333(22,400), 319(21,400), 305(17,300), 258(49,800), 235(46,600).

IR $\nu_{max}^{KBr}$cm$^{-1}$: 1780, 1720, 1690, 1655, 1625. (see, FIG. 1).

Figure 2:
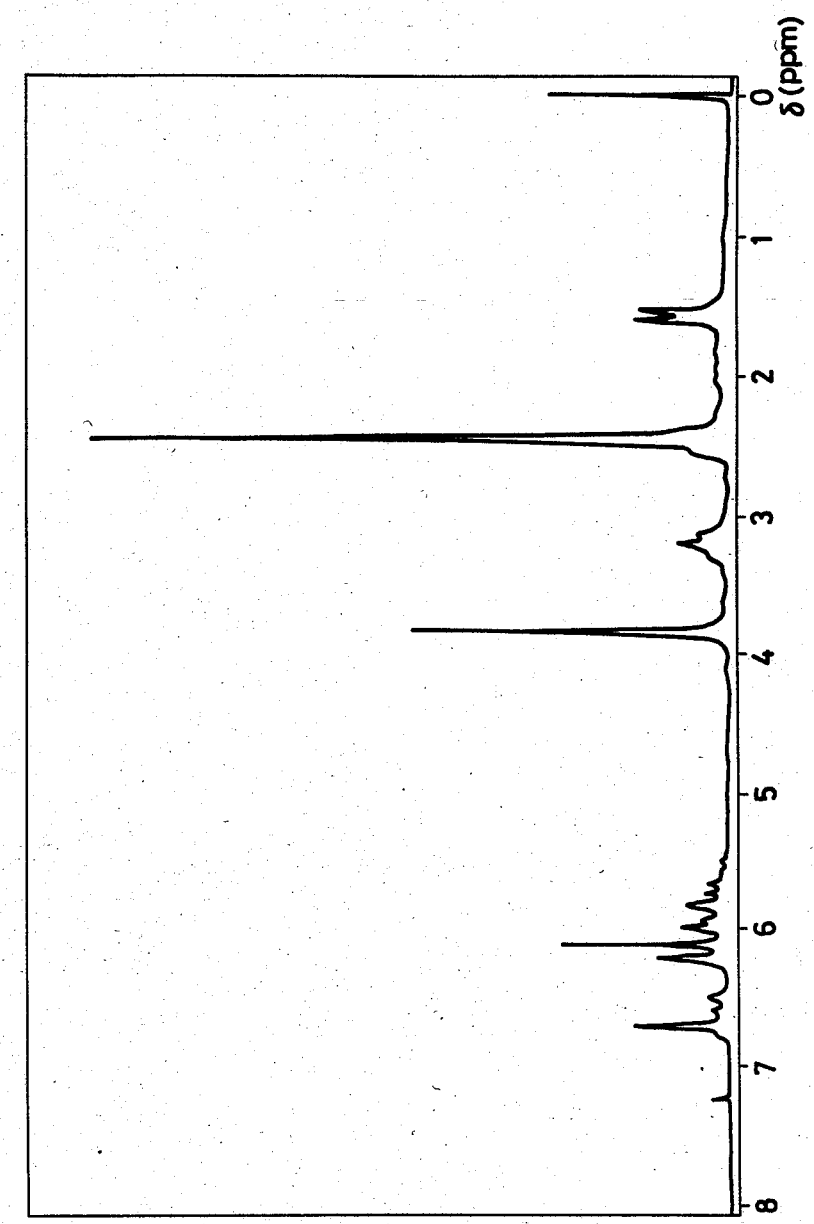

$^1$H-NMR δ ppm(CDCl$_3$): 12.02(br.s,1H), 10.32(br,1H), 3.84(s,3H), 3.21(t,2H), 2.45(s,6H), 1.56(d,3H). (See, FIG. 2).

EXAMPLE 2

Dissolved in 20 ml of pyridine was 0.54 g (1.0 mmol) of Fredericamycin A, to which 0.60 g (5.0 mmol) of isovaleryl chloride dissolved in 5 ml of pyridine was dropped with stirring at 0° C. over about 30 minutes. The resulting mixture was then stirred at 0° C. for 5 hours. The resultant liquid reaction mixture was poured into 200 ml of ice-cooled 2N hydrochloric acid, followed by an extraction with ethyl acetate. The ethyl acetate layer was washed successively with dilute hydrochloric acid and then with water, and was thereafter dried with anhydrous sodium sulfate. After filtration, the ethyl acetate was driven off under reduced pressure. One hundred milliliters of ether were added to the residue to crystallize a precipitate. The precipitate was collected by filtration and was then recrystallized from a mixed solvent of ethyl acetate, acetic acid and methanol to obtain 0.35 g of Fredericamycin A diisovalerate [R′=—COCH$_2$CH(CH$_3$)$_2$ in the formula (Ia); Compound 2] as yellowish brown crystals (yield: 49.5%).

Melting point: 260° C.

Mass M+ m/z: 707.

UV $\lambda_{max}^{EtOH}$nm(ε): 393(23,800), 374(33,700), 359(28,500), 333(23,500), 319(22,800), 305(19,900), 260(50,600), 235(44,000).

IR $\nu_{max}^{KBr}$cm$^{-1}$: 1775, 1720, 1690, 1655, 1620.

$^1$H-NMR δ ppm(CDCl$_3$): 12.04(br.s,1H), 9.82(br,1H), 6.76(s,1H), 6.64(m,1H), 6.25(s,1H), 6.11(s,1H), 6.2-5.5(m,3H), 3.83(s,3H), 3.22(t,2H), 2.8-2.0(m,8H), 1.60(d,3H), 1.09(d,12H).

EXAMPLE 3

Dissolved in 25 ml of pyridine was 0.54 g (1.0 mmol) of Fredericamycin A, to which 2.54 g (10 mmol) of p-methylbenzoic anhydride was added little by little with stirring at 0° C. After stirring the resultant mixture at 0° C. for 5 hours, it was allowed to stand at 0° C. for further 1 day. The resultant liquid reaction mixture was poured into 200 ml of ice-cooled 2N hydrochloric acid. The crystallized precipitate was collected by filtration, washed with water and then dried. This precipitate was washed twice with 100 ml of not isopropyl ether, and was then recrystallized from a mixed solvent of ethyl acetate, acetic acid and methanol to obtain 0.61 g of Fredericamycin A di-p-methylbenzoate

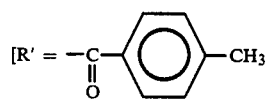

in the formula (Ia); Compound 3] as yellowish brown crystals (yield: 78.7%).

Melting point: over 300° C.

Mass M+ m/z: 775.

UV $\lambda_{max}^{EtOH}$nm(ε): 393(23,200), 374(34,200), 359(28,800), 333(23,700), 319(22,800), 305(18,900), 254(78,300).

IR $\nu_{max}^{KBr}$cm$^{-1}$: 1750, 1720, 1690, 1660, 1625.

$^1$H-NMR δ ppm(CDCl$_3$): 12.02(br,1H), 9.47(br,1H), 8.12(d,4H), 7.27(d,4H), 6.71(s,1H), 6.50(m,1H), 6.23(s,1H), 6.09(s,1H), 6.1-5.7(m,3H), 3.80(s,3H), 3.17(t,2H), 2.48(t,2H), 2.39(s,6H), 1.68(d,3H).

EXAMPLES 4-11

Similar to Examples 1-3, the following compounds were obtained. By the way, the compounds will be shown in terms of R' in the formula (Ia):

Compound 4

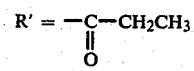

Melting point: over 300° C.
Appearance: Yellowish brown crystals.
Mass M+ m/z: 651.
UV $\lambda_{max}^{EtOH}$nm($\epsilon$): 393(22,100), 374(31,700), 359(26,200), 333(21,900), 319(21,200), 305(17,700), 258(51,200), 235(46,400).
IR $\nu_{max}^{KBr}$cm$^{-1}$: 1775, 1720, 1690, 1655, 1620.
$^1$H-NMR $\delta$ ppm(CDCl$_3$): 12.01(br.s,1H), 9.87(br,1H), 6.79(s,1H), 6.64(m,1H), 6.30(s,1H), 6.11(s,1H), 6.3-5.6(m,3H), 3.87(s,3H), 3.25(t,2H), 2.81(q,4H), 2.49(t,2H), 1.70(d,3H), 1.33(t,6H).

Compound 5

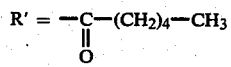

Melting point: 162°-164° C.
Appearance: Yellowish brown crystals.
Mass M+ m/z: 735.
UV $\lambda_{max}^{EtOH}$nm($\epsilon$): 393(23,300), 374(34,900), 359(29,200), 333(24,200), 319(23,300), 305(19,000), 258(53,800), 235(50,100).
IR $\nu_{max}^{KBr}$cm$^{-1}$: 1775, 1720, 1690, 1655, 1620.
$^1$H-NMR $\delta$ ppm(CDCl$_3$): 12.04(s,1H), 10.06(br.s,1H), 6.74(s,1H), 6.62(m,1H), 6.24(s,1H), 6.12(s,1H), 6.1-5.5(m,3H), 3.86(s,3H), 3.22(t,2H), 2.77(t,4H), 2.47(t,2H), 1.59(d,3H), 2.0-1.1(m,12H), 0.90(t,6H).

Compound 6

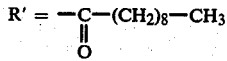

Melting point: 120°-122° C.
Appearance: Yellowish brown crystals.
Mass M+ m/z: 847.
UV $\lambda_{max}^{EtOH}$nm($\epsilon$): 393(23,600), 374(35,000), 359(29,300), 333(24,100), 319(22,800), 305(18,500), 260(54,000), 235(50,200).
IR $\nu_{max}^{KBr}$cm$^{-1}$: 1775, 1720, 1690, 1655, 1620.
$^1$H-NMR $\delta$ ppm(CDCl$_3$): 12.00(br.s,1H), 10.27(br,1H), 6.70(s,1H), 6.64(m,1H), 6.23(s,1H), 6.12(s,1H), 6.1-5.4(m,3H), 3.86(s,3H), 3.21(t,2H), 2.77(t,4H), 2.47(t,2H), 1.51(d,3H), 2.0-1.1(m,28H), 0.84(t,6H).

Compound 7

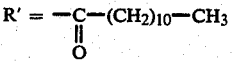

Melting point: 112°-114° C.
Appearance: Yellowish brown crystals.
Mass M+ m/z: 903.
UV $\lambda_{max}^{EtOH}$nm($\epsilon$): 393(23,100), 374(34,100), 359(28,600), 333(23,500), 319(22,200), 305(18,200), 260(53,500), 235(49,500).
IR $\nu_{max}^{KBr}$cm$^{-1}$: 1775, 1720, 1690, 1655, 1625.
$^1$H-NMR $\delta$ ppm(CDCl$_3$): 12.02(br,1H), 10.16(br,1H), 6.74(s,1H), 6.63(m,1H), 6.24(s,1H), 6.11(s,1H), 6.1-5.5(m,3H), 3.85(s,3H), 3.22(t,2H), 2.76(t,4H), 2.47(t,2H), 1.58(d,3H), 2.0-1.0(m,36H), 0.86(t,6H).

Compound 8

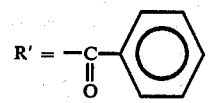

Melting point: over 300° C.
Appearance: Yellowish brown crystals.
Mass M+ m/z: 747.
UV $\lambda_{max}^{EtOH}$nm($\epsilon$): 393(24,000), 374(35,400), 359(29,700), 333(24,700), 319(24,100), 305(20,000), 255(64,900), 237(70,000).
IR $\nu_{max}^{KBr}$cm$^{-1}$: 1750, 1720, 1690, 1655, 1625.
$^1$H-NMR $\delta$ ppm(CDCl$_3$): 12.08(br,1H), 9.23(br,1H), 8.24(br.d,4H), 7.7-7.3(m,6H), 6.74(s,1H), 6.60(m,1H), 6.25(s,1H), 6.11(s,1H), 6.1-5.6(m,3H), 3.81(s,3H), 3.19(t,2H), 2.49(t,2H), 1.73(d,3H).

Compound 9

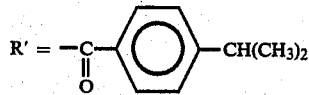

Melting point: over 300° C.
Appearance: Yellowish brown crystals.
Mass M+ m/z: 831.
UV $\lambda_{max}^{EtOH}$nm($\epsilon$): 393(23,800), 374(35,100), 359(29,500), 333(24,600), 319(23,600), 305(19,800), 254(81,700).
IR $\nu_{max}^{KBr}$cm$^{-1}$: 1750, 1720, 1690, 1660, 1625.
$^1$H-NMR $\delta$ ppm(CDCl$_3$): 12.08(br,1H), 9.66(br,1H), 8.16(d,4H), 7.32(d,4H), 6.70(s,1H), 6.61(m,1H), 6.22(s,1H), 6.10(s,1H), 6.1-5.6(m,3H), 3.80(s,3H), 3.16(t,2H), 2.95(m,2H), 2.48(t,2H), 1.66(d,3H), 1.26(d,12H).

Compound 10

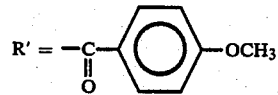

Melting point: over 300° C.
Appearance: Yellowish brown crystals.
Mass M+ m/z: 807.
UV $\lambda_{max}^{EtOH}$nm($\epsilon$): 393(23,100), 374(33,600), 359(28,300), 333(23,600), 319(22,800), 304(20,700), 263(85,700).
IR $\nu_{max}^{KBr}$cm$^{-1}$: 1740, 1720, 1690, 1655, 1620, 1605.
$^1$H-NMR $\delta$ ppm(CDCl$_3$): 12.04(br,1H), 9.86(br,1H), 8.19(d,4H), 6.95(d,4H), 6.67(s,1H), 6.62(m,1H), 6.20(s,1H), 6.09(s,1H), 6.1–5.6(m,3H), 3.82(s,6H), 3.79(s,3H), 3.15(t,2H), 2.47(t,2H), 1.61(d,3H).

Compound 11

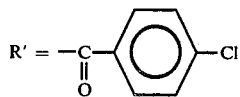

Melting point: over 300° C.
Appearance: Yellowish brown crystals.
Mass M+ m/z: 815, 817, 819.
UV $\lambda_{max}^{EtOH}$nm($\epsilon$): 393(24,300), 374(36,200), 359(30,800), 333(25,800), 319(24,900), 305(20,800), 253(87,200).
IR $\nu_{max}^{KBr}$cm$^{-1}$: 1750, 1720, 1690, 1655, 1625.
$^1$H-NMR $\delta$ ppm(CDCl$_3$): 12.10(br,1H), 9.40(br,1H), 8.17(d,4H), 7.45(d,4H), 6.74(s,1H), 6.60(m,1H), 6.24(s,1H), 6.10(s,1H), 6.1–5.6(m,3H), 3.82(s,3H), 3.17(t,2H), 2.48(t,2H), 1.69(d,3H).

EXAMPLE 12

Dissolved in 30 ml of tetrahydrofuran was 0.50 g of Fredericamycin A, followed by an addition of 0.05 g of 10% palladium carbon. Fredericamycin A was subjected with stirring to catalytic reduction at room temperature. After proceeding with the reaction for 10 hours, 10 ml of pyridine and 1 ml of acetic anhydride were added to the liquid reaction mixture under nitrogen gas stream. The resultant mixture was stirred at room temperature for further 1 hour. The resultant liquid reaction mixture was filtered, and the filtrate was added with stirring into ice-cooled n-hexane. The resultant precipitate was collected by filtration. The precipitate was recrystalized from a mixed solvent of chloroform and ethyl acetate to obtain 0.53 g of leucotetraacetyltetrahydrofredericamycin A [R'=—COCH$_3$ in the formula (Ib); Compound 12] as yellow crystals (yield: 80%).
Melting point: 273° C. (decomposed).
UV $\lambda_{max}^{dioxane}$nm($\epsilon$): 241(51,300), 287(68,400), 338(17,100), 352(20,000).
IR $\nu_{max}^{KBr}$cm$^{-1}$: 1780, 1740, 1715, 1660, 1650, 1620.
$^1$H-NMR $\delta$ ppm(DMSO d-6): 12.96(s,1H), 11.52(s,1H), 7.87(s,1H), 6.90(s,1H), 6.35(s,1H), 3.96(s,3H), 3.16(t,2H), 2.5(m,4H), 2.44(s,12H), 1.8–1.1(m,6H), 0.80(t,3H).
Mass M+ m/z: 713.
Anal. Calcd. For C$_{38}$H$_{35}$NO$_{13}$: C, 63.95; h, 4.94; N, 1.96. Found: C, 63.93; H, 4.95; N, 1.93.

EXAMPLES 13–16

Similar to Example 12, the following compounds were also obtained. The compounds will be expressed in terms of R' in the formula (Ib).

Compound 13

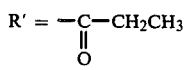

Melting point: 255°–256° C.
Appearance: Yellow crystals.
UV $\lambda_{max}^{dioxane}$nm($\epsilon$): 238(51,300), 287(64,900), 338(15,900), 352(19,000).

Figure 3:
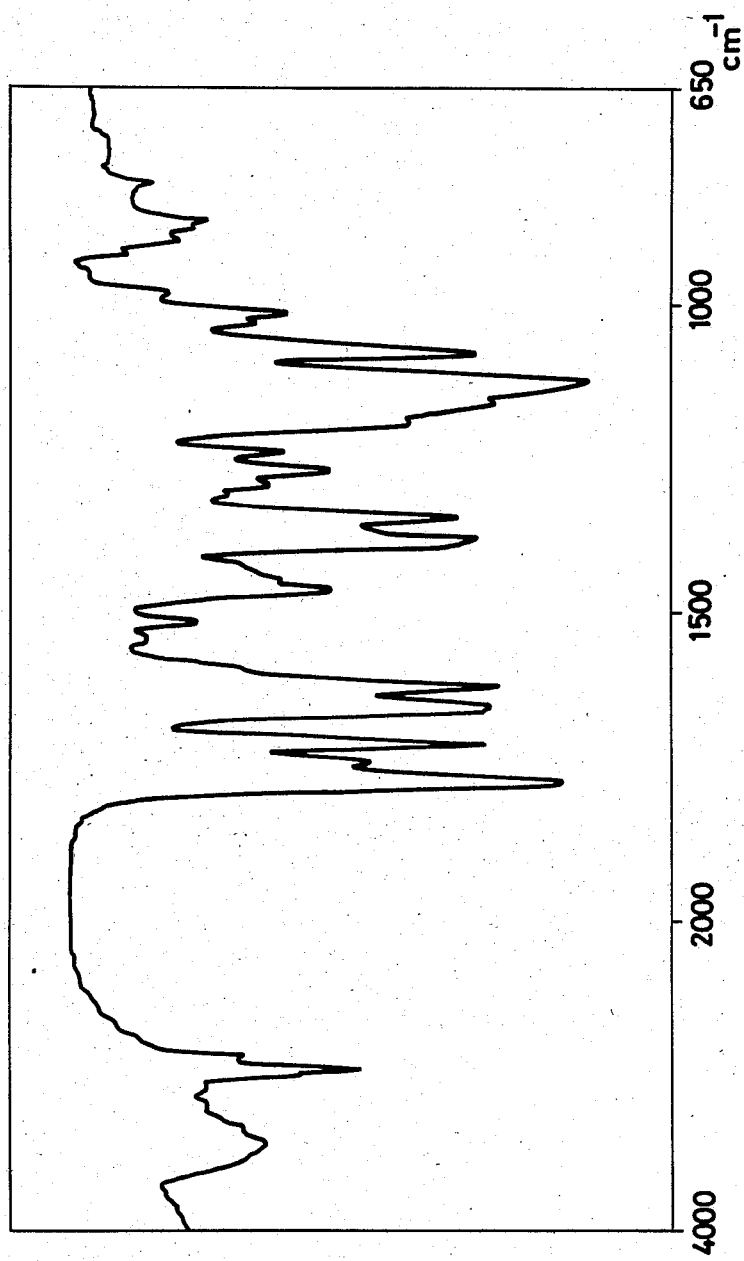
FIG. 3 and FIG. 4 illustrate an IR and $^1$H-NMR spectra of Compound 13, respectively.
Figure 4:
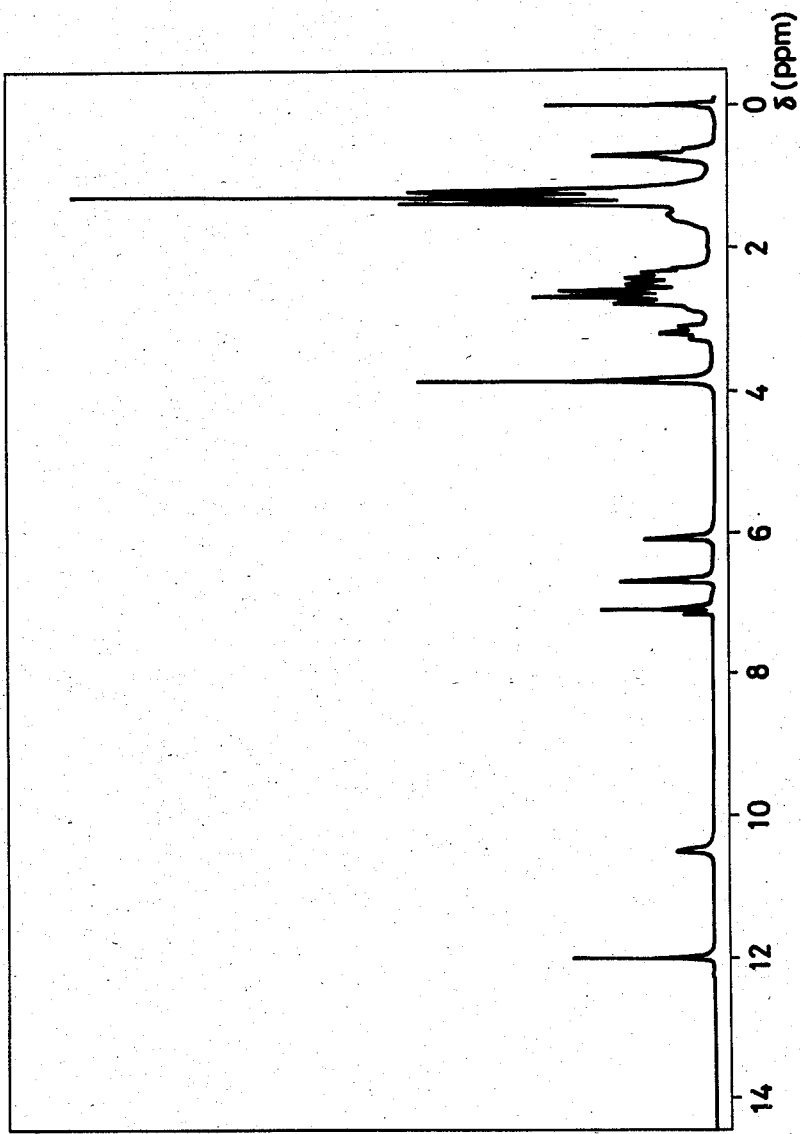

IR $\nu_{max}^{KBr}$cm$^{-1}$: 1780, 1745, 1715, 1660, 1655, 1620. (see, FIG. 3).
$^1$H-NMR $\delta$ ppm(CDCl$_3$): 12.02(s,1H), 10.48(br.s,1H), 7.15(s,1H), 6.75(s,1H), 6.14(s,1H), 3.89(s,3H), 3.21(t,2H), 2.67(q,8H), 2.42(m,4H), 1.7–1.1(m,6H), 1.31(t,12H), 0.73(t,3H). (see, FIG. 4).
Mass M+ m/z: 769.

Compound 14

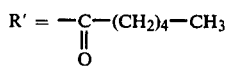

Melting point: 175°–176° C.
Appearance: Yellow crystals.
UV $\lambda_{max}^{dioxane}$nm($\epsilon$): 238(52,700), 287(65,600), 338(16,100), 352(19,100).
IR $\nu_{max}^{KBr}$cm$^{-1}$: 1780, 1745, 1715, 1660, 1655, 1620.
$^1$H-NMR $\delta$ ppm(CDCl$_3$): 11.98(s,1H), 10.44(br.s,1H), 7.13(s,1H), 6.75(s,1H), 6.14(s,1H), 3.89(s,3H), 3.21(t,2H), 2.63(t,8H), 2.43(m,4H), 2.0–0.7(m,42H), 0.72(t,3H).

Compound 15

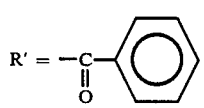

Melting point: 229°–230° C.
Appearance: Yellow crystals.
UV $\lambda_{max}^{dioxane}$nm($\epsilon$): 236(82,200), 287(69,800), 339(16,900), 352(20,300).
IR $\nu_{max}^{KBr}$cm$^{-1}$: 1750, 1715, 1660, 1650, 1620.
$^1$H-NMR $\delta$ ppm(CDCl$_3$): 12.00(br.s,1H), 9.70(br,1H), 7.89(d,8H), 7.33(s,1H), 7.06(m,12H), 6.63(s,1H), 6.07(s,1H), 3.90(s,3H), 3.10(t,2H), 2.41(m,4H), 1.7–1.0(m,6H), 0.79(t,3H).

Compound 16

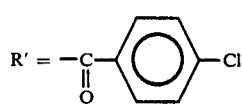

Melting point: over 300° C.
Appearance: Yellow crystals.
UV $\lambda_{max}^{dioxane}$nm ($\epsilon$): 242(101,400), 286(73,500), 338(17,800), 352(21,200).
IR $\nu_{max}^{KBr}$cm$^{-1}$: 1750, 1720, 1660, 1650, 1620.
$^1$H-NMR $\delta$ ppm (CDCl$_3$): 12.06(br,1H), 9.12(br,1H), 7.81(d,8H), 7.34(s,1H), 7.11(d,8H), 6.68(s,1H), 6.10(s,1H), 3.93(s,3H), 3.14(t,2H), 2.43(m,4H), 1.7–1.1(m,6H), 0.82(t,3H).

EXAMPLE 17

Dissolved in 30 ml of tetrahydrofuran was 0.50 g of Fredericamycin A, followed by an addition of 0.07 g of 10% palladium carbon. Fredericamycin A was then subjected with stirring to catalytic reduction at room temperature. After proceeding with the reaction for 10 hours, the crystallized yellow reductant was taken up in a mixed solvent of chloroform and methanol. The palladium carbon was removed by filtration, and a small amount of dimethylsulfoxide was added to the filtrate.

The resultant mixture was then stirred for 3 hours at room temperature. The deposited red crystals were collected by filtration and were then recrystallized from a mixed solvent of chloroform and methanol to obtain 0.29 g of tetrahydrofredericamycin A [R=H in the formula (Ic); Compound 17] as red crystals (yield: 60%).

Figure 5:
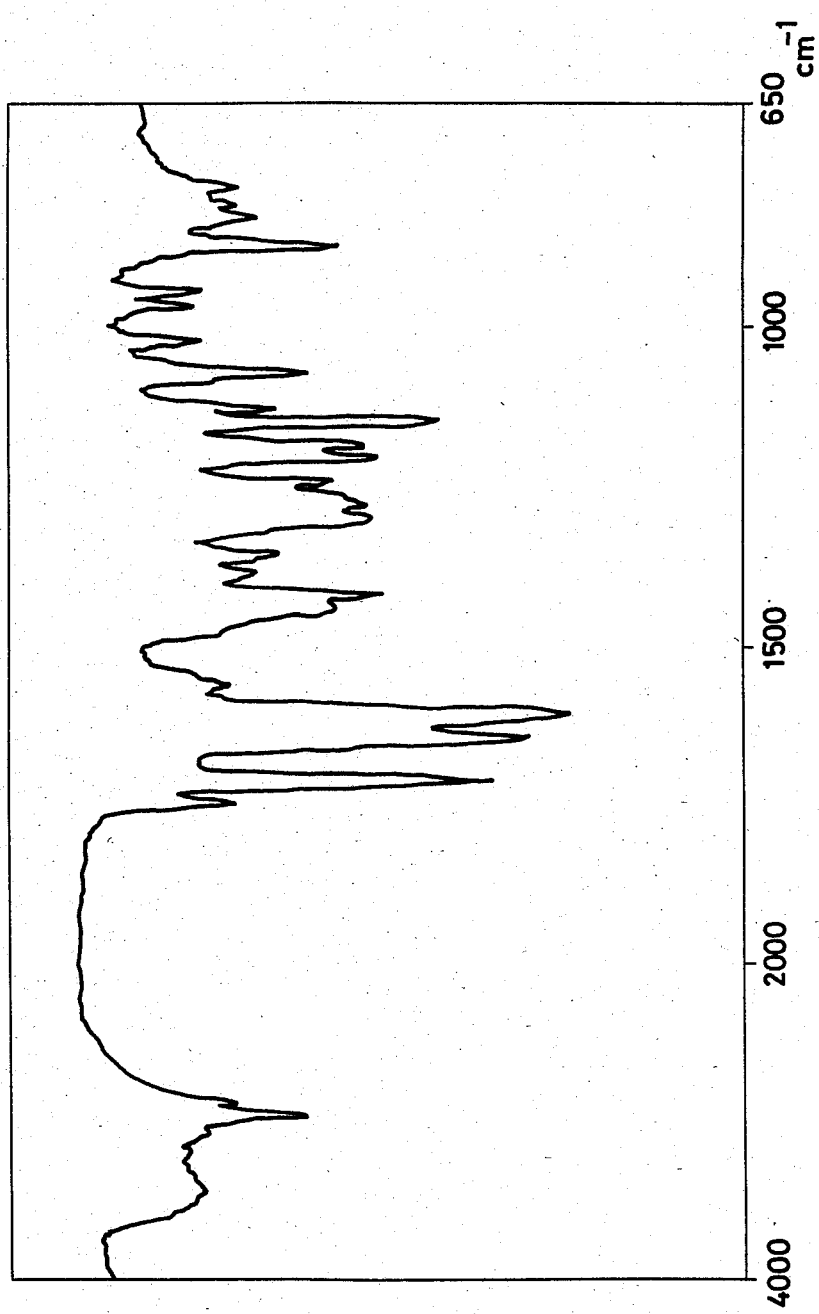
FIG. 5 and FIG. 6 depict an IR and $^1$H-NMR spectra of Compound 17, respectively.
Figure 6:
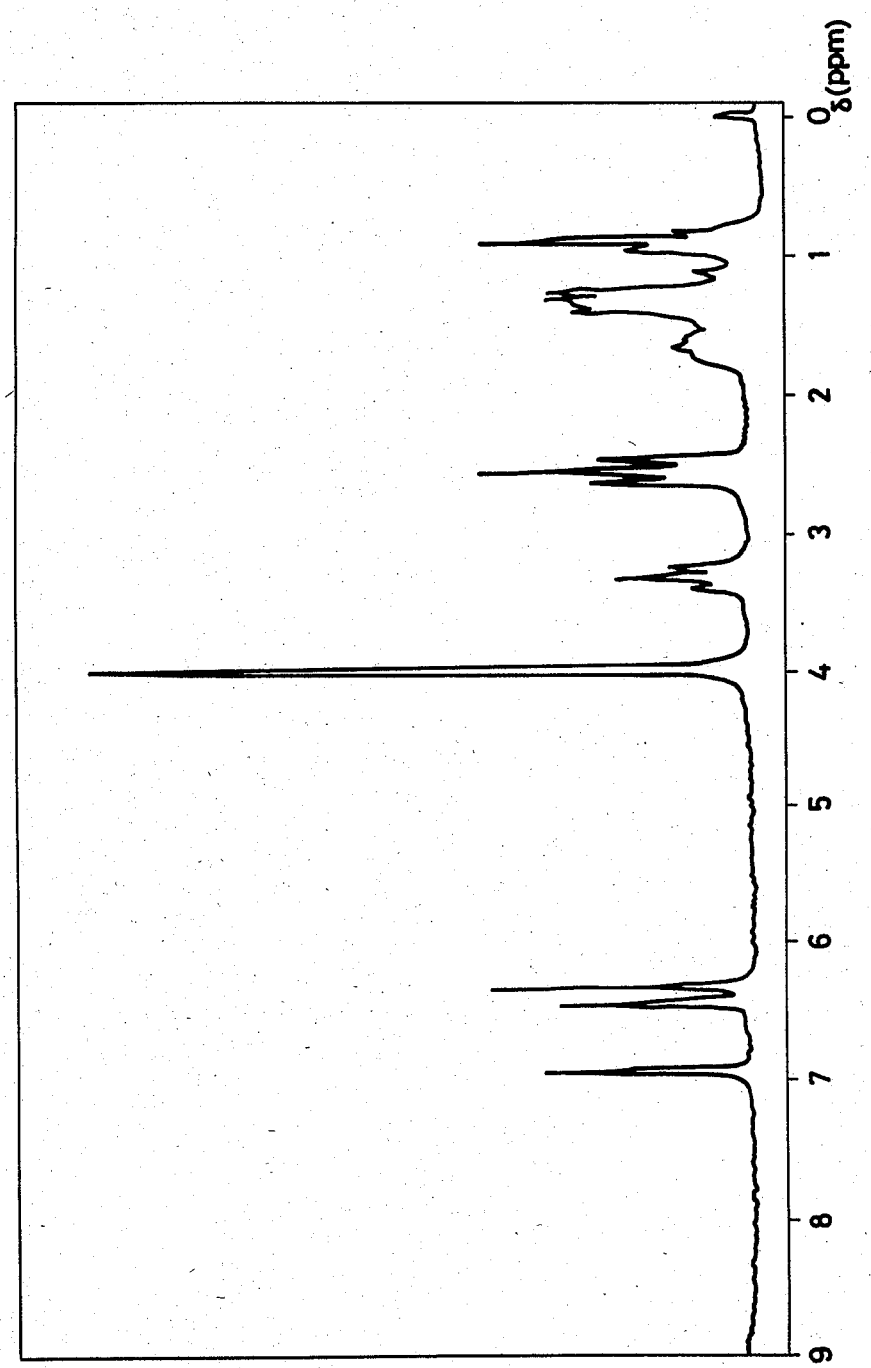

Melting point: over 300° C.
UV $\lambda_{max}^{dioxane}$nm($\epsilon$): 243(69,000), 285(18,500), 298(18,900), 322(9,500), 337(11,400), 353(10,600), 507(10,600).
IR $\nu_{max}^{KBr}$cm$^{-1}$: 1750, 1720, 1650, 1610. (see, FIG. 5).
$^1$H-NMR $\delta$ ppm[CDCl$_3$-CF$_3$COOD(10:1)]: 6.96(s,1H), 6.44(s,1H), 6.32(s,1H), 3.96(s,3H), 3.32(t,2H), 2.55(t,4H), 1.8-1.1(m,6H), 0.88(t,3H). (see, FIG. 6).
Mass M+ m/z: 543.
Anal. Calcd. for C$_{30}$H$_{25}$NO$_9$ (m.w. 543.53): C, 66.29; H, 4.63; N, 2.58. Found: C, 66.11; H, 4.65; N, 2.57.

EXAMPLE 18

Dissolved in 6 ml of pyridine was 0.25 g of tetrahydrofredericamycin A, followed by an addition of 0.5 ml of acetic anhydride. The mixture was stirred at 0°-4° C. for 1 hour. The resulting liquid reaction mixture was added with stirring into ice-cooled n-hexane. The resulting precipitate was collected by filtration and was then dried. The precipitate was thereafter recrystallized from a mixed solvent of ethyl acetate and acetic acid to obtain 0.26 g of diacetyltetrahydrofredericamycin A

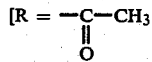

in the formula (Ic); Compound 18] as crystals of a light orange-yellow color (yield: 90%).

Figure 7:
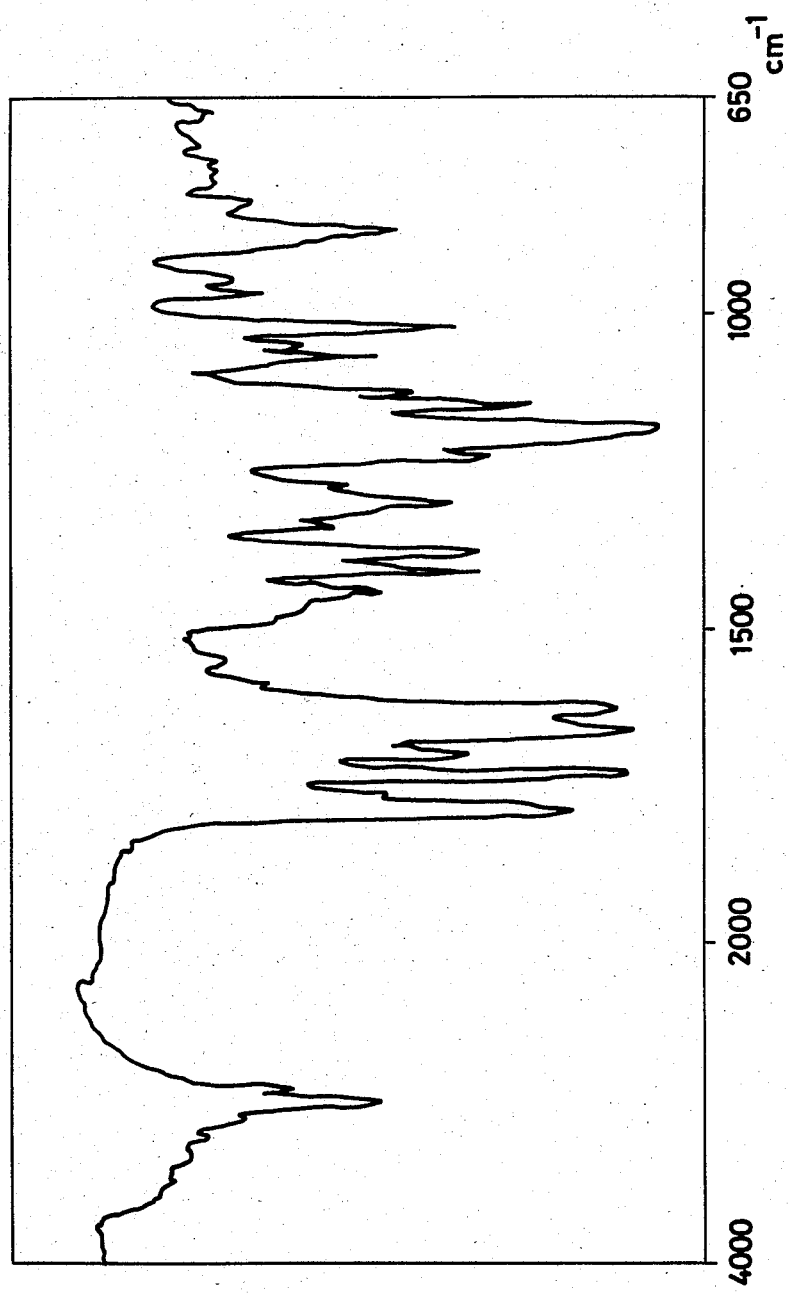
FIG. 7 and FIG. 8 show an IR and $^1$H-NMR spectra of Compound 18, respectively.
Figure 8:
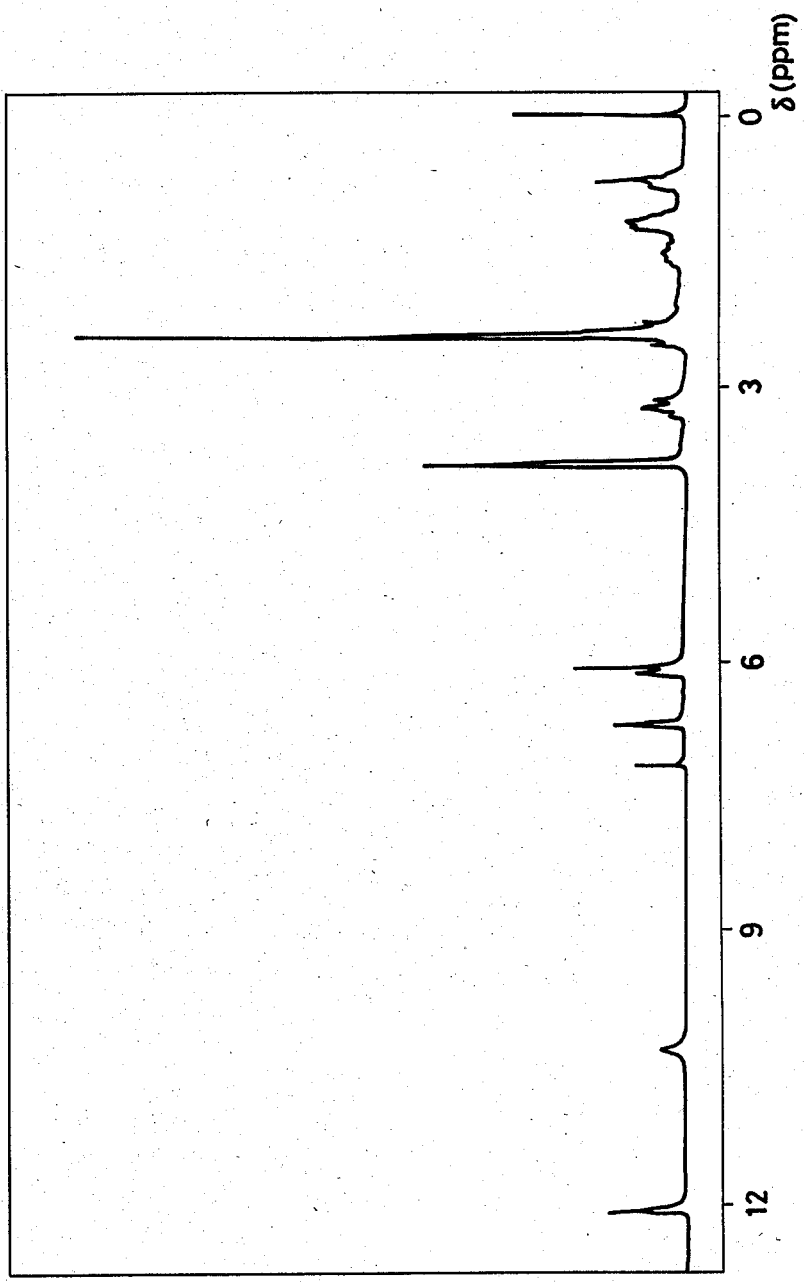

Melting point: 265° C. (decomposed).
UV $\lambda_{max}^{dioxane}$nm($\epsilon$): 238(67,700), 323(sh), 338(15,700), 352(17,600).
IR $\nu_{max}^{KBr}$cm$^{-1}$: 1785, 1760, 1725, 1690, 1660, 1620. (see, FIG. 7).
$^1$H-NMR $\delta$ ppm(CDCl$_3$): 12.06(s,1H), 10.27(s,1H), 6.75(s,1H), 6.14(s,1H) 6.10(s,1H), 3.85(s,3H), 3.25(t,2H), 2.50(m,4H), 2.44(s,6H), 1.8-1.1(m,6H), 0.76(t,3H). (see, FIG. 8).
Mass M+ m/z: 627.
Anal. Calcd. for C$_{34}$H$_{29}$NO$_{11}$: C, 65.07; H, 4.66; N, 2.23. Found: C, 65.11; H, 4.65; N, 2.18.

EXAMPLES 19-23

Similar to Example 18, the following compounds were obtained. The compounds will be expressed in terms of R of the formula (Ic).

Compound 19

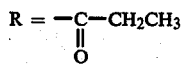

Melting point: 278°-279° C.
Appearance: Crystals of a light orange-yellow color.
UV $\lambda_{max}^{dioxane}$nm($\epsilon$): 237(59,500), 338(13,800), 352(15,100).
IR $\nu_{max}^{KBr}$cm$^{-1}$: 1780, 1760, 1725, 1690, 1660, 1625.
$^1$H-NMR $\delta$ ppm(CDCl$_3$): 12.08(s,1H), 10.20(br.s,1H), 6.81(s,1H), 6.20(s,1H), 6.15(s,1H), 3.90(s,3H), 3.28(t,2H), 2.83(q,4H), 2.45(m,4H), 1.7-1.1(m,6H), 1.35(t,6H), 0.77(t,3H).
Mass M+ m/z: 655.

Compound 20

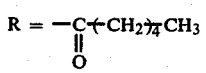

Melting point: 254°-255° C.
Appearance: Crystals of a light orange-yellow color.
UV $\lambda_{max}^{dioxane}$nm($\epsilon$): 237(66,800), 339(14,600), 353(16,200).
IR $\nu_{max}^{KBr}$cm$^{-1}$: 1780, 1760, 1725, 1690, 1660, 1625.
$^1$H-NMR $\delta$ ppm(CDCl$_3$): 12.07(s,1H), 10.74(s,1H), 6.73(s,1H), 6.14(s,2H), 3.88(s,3H), 3.24(t,3H), 2.79(t,4H), 2.44(m,4H), 2.0-1.0(m,18H), 0.91(t,6H), 0.73(t,3H).
Mass M+ m/z: 739.

Compound 21

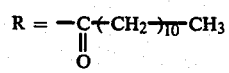

Melting point: 216°-217° C.
Appearance: Crystals of a light orange-yellow color.
UV $\lambda_{max}^{dioxane}$nm($\epsilon$): 237(63,000), 339(13,700), 353(15,100).
IR $\nu_{max}^{KBr}$cm$^{-1}$: 1780, 1760, 1725, 1690, 1655, 1625.
$^1$H-NMR $\delta$ ppm(CDCl$_3$): 12.13(s,1H), 10.08(br.1H), 6.79(s,1H), 6.19(s,1H), 6.13(s,1H), 3.88(s,3H), 3.27(t,2H), 2.78(t,4H), 2.45(m,4H), 2.0-0.9(m,42H), 0.87(t,6H), 0.78(t,3H).

Compound 22

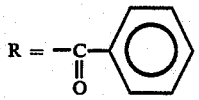

Melting point: 290°-292° C.
Appearance: Crystals of a light orange-yellow color.
UV $\lambda_{max}^{dioxane}$nm($\epsilon$): 239(79,700), 338(14,200), 352(15,200).
IR $\lambda_{max}^{KBr}$cm$^{-1}$: 1755, 1725, 1690, 1655, 1625.
$^1$H-NMR $\delta$ ppm (CDCl$_3$): 12.10(br.s1H), 8.70(br,1H), 8.22(d,4H), 7.56(m,6H), 6.74(s,1H), 6.14(s,1H), 6.10(s,1H), 3.84(s,3H), 3.22(t,2H), 2.45(m,4H), 1.7-1.0(m,6H), 0.83(t,3H).
Mass M+ m/z: 751.

Compound 23

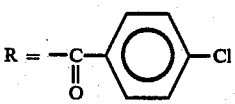

Melting point: 289°-290° C.
Appearance: Crystals of a light orange-yellow color.
UV $\lambda_{max}^{dioxane}$nm($\epsilon$): 245(93,900), 338(15,000), 352(16,400).
IR $\nu_{max}^{KBr}$cm$^{-1}$: 1755, 1725, 1690, 1655, 1625.
$^1$H-NMR $\delta$ ppm(CDCl$_3$): 12.16(br,1H), 10.20(br,1H), 8.18(d,4H), 7.47(d,4H), 6.73(s,1H), 6.14(s,2H), 3.84(s,3H), 3.22(t,2H), 2.45(m,4H), 1.7–1.1(m,6H), 0.77(t,3H).

Mass M+ m/z: 819, 821, 823.

REFERENCE EXAMPLE

Streptomyces sp.S 9816 (FRI Deposition FERM BP-561; Date of Deposition: Jan. 26, 1983), a Fredericamycin A producing microorganism, was inoculated on a liquid culture medium containing 4.0% of soluble starch, 4.0% of glucose, 1.0% of Soyton (Difco Corp.), 1.0% of yeast extract, 0.25% of sodium chloride, 0.32% of calcium carbonate, 0.0005% of copper sulfate, 0.0005% of manganese chloride and 0.005% of zinc sulfate (pH: 7.0). The microorganism was cultured with shaking at 27° C. for 2 days to prepare a seed culture. Charged in a Sakaguchi flask having an internal volume of 500 ml was 120 ml of a liquid culture medium of the same composition as that used above, to which 0.6 ml of the above-prepared seed culture was inoculated. On a reciprocally-shaking culture machine, the seed culture was cultured for 7 days under the following conditions:

Amplitude: 9 cm
Revolution speed: 110 r.p.m.
Culture temperature: 27° C.

After completion of the culture, dilute hydrochloric acid was added to 10 liters of the resulting liquid culture to adjust its pH to 2.0. Thereafter, 20 liters of a 1:1 mixed solvent of methanol and chloroform were added to the liquid culture. The resultant mixture were stirred thoroughly to extract the culture with the mixed solvent. This procedure was repeated twice. The resulting chloroform layers were collected and were then concentrated under reduced pressure. The resultant concentrate was washed with a small amount of n-hexane and was then dried to obtain 8.1 g of red powder. Then, the above red powder was dissolved in chloroform which contained 1% of acetic acid. The thus-prepared solution was then caused to pass through a column which contained 800 g of Kiesel Gel 60 (product of Merck % Co. Inc.) and had been filled in advance with chloroform containing 1% acetic acid. The column was then eluted with the same solvent. Fredericamycin A fractions were collected, and the eluate was concentrated under reduced pressure. The concentrate was allowed to stand at a cool place, thereby allowing about 5.0 g of Fredericamycin A to deposit as fine crystals of a dark purple color.

What is claimed is:

1. A Fredericamycin A derivative of formula (I):

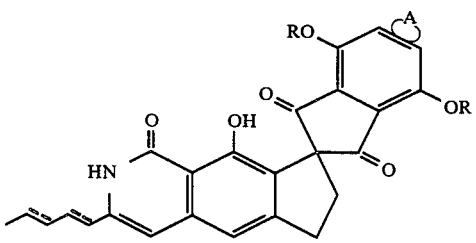

wherein R is a hydrogen atom or a C-acyl group, A denotes

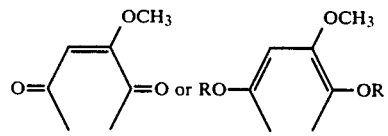

and the dotted lines in the formula indicated optional double bonds, with the proviso that when A is

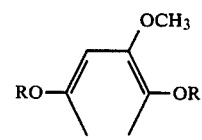

or when the optional double bonds are present in the formula, group R is a group other than a hydrogen atom.

2. The Fredericamycin A derivative of claim 1, wherein said C-acyl group is of the formula: $R_1$—CO—, wherein $R_1$ is a substituted or unsubstituted phenyl group, or a $C_{1-18}$ straight- or branched chain alkyl group.

3. The Fredericamycin A derivative of claim 2, wherein the substituent on said phenyl group is selected from the group consisting of halogen, lower alkyl containing from 1–6 carbon atoms and lower alkoxy containing from 1–6 carbon atoms.

4. A Fredericamycin A diacyl derivative of formula (Ia):

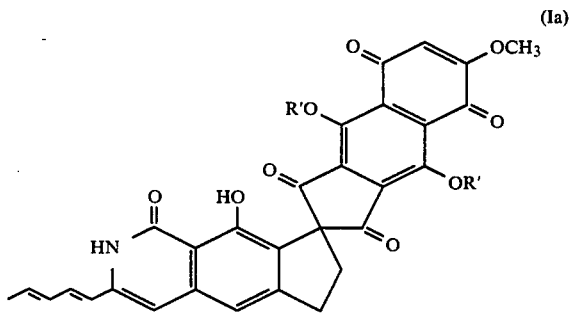

wherein R' is a C-acyl group.

5. The Fredericamycin A derivative of claim 4, wherein said C-acyl group is of the formula: $R_1$—CO—, wherein $R_1$ is a substituted or unsubstituted phenyl group, or a $C_{1-18}$ straight- or branched chain alkyl group.

6. The Fredericamycin A derivative of claim 5, wherein the substituent on said phenyl group is selected from the group consisting of halogen, lower alkyl containing from 1–6 carbon atoms and lower alkoxy containing from 1–6 carbon atoms.

7. A leucotetraacyltetrahydrofredericamycin A derivative of formula (Ib):

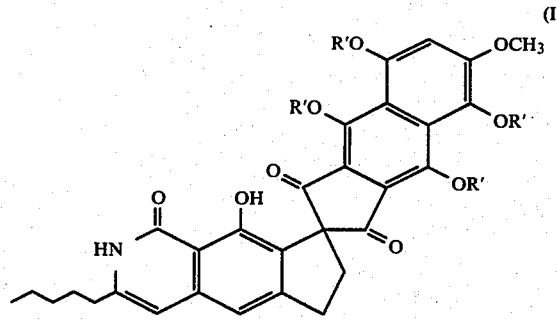

(Ib)

wherein R' is a C-acyl group.

8. The Fredericamycin A derivative of claim 7, wherein said C-acyl group is of the formula: $R_1$—CO—, wherein $R_1$ is a substituted or unsubstituted phenyl group, or a $C_{1-18}$ straight- or branched chain alkyl group.

9. The Fredericamycin A derivative of claim 8, wherein the substituent on said phenyl group is selected from the group consisting of halogen, lower alkyl containing from 1–6 carbon atoms and lower alkoxy containing from 1–6 carbon atoms.

10. A tetrahydrofredericamycin A derivative of formula (Ic):

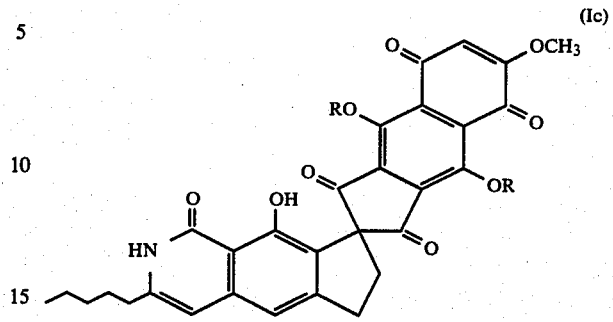

(Ic)

wherein R is a hydrogen atom or a C-acyl group.

11. The Fredericamycin A derivative of claim 10, wherein said C-acyl group is of the formula: $R_1$—CO—, wherein $R_1$ is a substituted or unsubstituted phenyl group, or a $C_{1-18}$ straight- or branched chain alkyl group.

12. The Fredericamycin A derivative of claim 11, wherein the substituent on said phenyl group is selected from the group consisting of halogen, lower alkyl containing from 1–6 carbon atoms and lower alkoxy containing from 1–6 carbon atoms.

* * * * *